US00PP12724P2

(12) United States Plant Patent
van der Voort

(10) Patent No.: US PP12,724 P2
(45) Date of Patent: Jun. 25, 2002

(54) LILY PLANT NAMED 'LOMBARDIA'

(75) Inventor: Cees A. van der Voort, Katwijk (NL)

(73) Assignee: Vletter & Den Haan Beheer B.V., Rijnsburg (NL)

( * ) Notice: Subject to any disclaimer, the term of this patent is extended or adjusted under 35 U.S.C. 154(b) by 0 days.

(21) Appl. No.: 09/357,101

(22) Filed: Jul. 19, 1999

(51) Int. Cl.[7] ..... A01H 5/00
(52) U.S. Cl. ..... Plt./315
(58) Field of Search ..... Plt./315

(56) References Cited

PUBLICATIONS

Plant Breeder's Rights application in The Netherlands (Nov. 16, 1991).
Plant Breeder's Rights denomination in The Netherlands (Mar. 16, 1993).
Plant Breeder's Rights certificate in The Netherlands (Mar. 16, 1993).

UPOV–ROM GTITM Computer Database 2000/02, GTI Jouve Retrieval Software, citation for 'Lombardia', 1991..* http://www.user.netland.nl/~hanns//exit4.html, p. 2, May 1996.*

* cited by examiner

*Primary Examiner*—Bruce R. Campell
*Assistant Examiner*—Anne Marie Grünberg
(74) *Attorney, Agent, or Firm*—Foley & Lardner

(57) ABSTRACT

A new and distinct cultivar of Lily plant named 'Lombardia' characterized by having light pink flowers, contrasting yellow mid-vein, and contrasting orange pollen.

1 Drawing Sheet

BACKGROUND OF THE INVENTION

The present invention comprises a new and distinct cultivar of lily plant, botanically known as *Lilium L.*, and hereinafter referred to by the cultivar name 'Lombardia'.

'Lombardia' is a product of a planned breeding program which had the objective of creating new lily cultivars having large, upright, pink flowers.

'Lombardia' was originated from a hybridization made by the inventor in a controlled breeding program in Rijnsburg, the Netherlands in 1983. The male and female parents were unnamed seedlings of *Lilium L.* oriental hybrids. Both parents are proprietary cultivars used in the breeding program.

'Lombardia' was discovered and selected as one flowering plant within the progeny of the stated cross by the inventor, Cees A. van der Voort, on Jun. 7, 1983 in a controlled environment in Rijnsburg, the Netherlands.

The first act of asexual reproduction of 'Lombardia' was accomplished when scales were taken from the initial selection in October 1986 in a controlled environment in Rijnsburg, the Netherlands by, or under the supervision of, Cees A. van der Voort. Horticultural examination of selected units initiated in May, 1986 has demonstrated that the combination of characteristics as herein disclosed for 'Lombardia' are firmly fixed and are retained through successive generations of asexual reproduction.

BRIEF DESCRIPTION OF THE INVENTION

The following traits have been repeatedly observed and are determined to be basic characteristics of 'Lombardia' which in combination distinguish this lily as a new and distinct cultivar:

1. Light pink flowers;
2. Contrasting yellow mid-vein; and
3. Contrasting orange pollen.

'Lombardia' has not been observed under all possible environmental conditions. The phenotype of the new cultivar may vary significantly with variations in environment such as temperature, light intensity, and daylength without any change in genotype. The following observations, measurements, and comparisons describe plants grown in greenhouse/field conditions at the Dutch experimental testing station CPRO-DLO, Wageningen, the Netherlands under conditions which approximate those generally used in commercial practice.

Of the many commercial cultivars known to the present inventor, no other cultivars are similar in comparison to 'Lombardia'.

BRIEF DESCRIPTION OF THE DRAWING

The accompanying color photographic drawing shows typical plant, and flower characteristics of 'Lombardia', with colors being as true as possible with illustrations of this type.

DETAILED BOTANICAL DESCRIPTION

In the following description, color references are made to The Royal Horticultural Society Colour Chart (R.H.S.). The color values were determined between 12 am and 2 pm on Nov. 16, 1992 at the Dutch experimental research station CPRO-DLO, Wageningen, the Netherlands.

Origin: Seedling from breeding program.
Parentage:
*Female paren.*—Unnamed seedling.
*Male parent.*—Unnamed seedling.

Classification:

*Botanical.*—A hybrid of the genus *Lilium L.*

*Commercial.*—Oriental Lily cv. 'Lombardia'.

Plant:

*Form.*—A single stem carrying numerous, alternately arranged pedicels.

*Height.*—Medium to high for the mature plant, approximately 120 cm, depending on cultivation conditions.

*Growth habit.*—Vigorous i.e., approximately 20–30% more vigorous than the traditional 'Stargazer' cultivar.

*Stem.*—Circular in transverse section; anthocyanin pigmentation absent; internodal length 6.5 cm, depending on the cultivation conditions of the cultivar.

*Foliage.*—Quantity: Approximately 65, depending on cultivation conditions. Size of leaf: Average length is 20–22 cm, average width is 2.5–3.5 cm, depending on cultivation conditions. Shape of leaf: Generally ovate, hardly any pubescence. Color: Medium green RHS 135B.

*Bulb.*—Size: 16 to 18 cm in circumference. Color: White RHS 157B with pink shades.

Bud:

*Form.*—Tapering like a lancet.

*Size.*—Medium, 11 cm in length depending on cultivation conditions.

*Opening.*—Unfolds normally.

*Color.*—Light pink, RHS 63D, fading to greenish yellow.

*Tepals.*—Folded, three visible.

Flower:

*Blooming habit.*—Raceme.

*Size.*—Medium, 20 cm diameter, depending on cultivation conditions.

*Borne.*—Horizontal along a longitudinal axis.

*Shape.*—Generally, hexagonal star if form and bowl-shaped in cross section.

*Tepalage.*—Number of Tepals: 6. Arrangement: Three inner and three outer. Color: Upper Surface: Pink, RHS 65A, but slightly bluish; RHS 104D, as is a typical characteristic of this cultivar and is visible when the daylight strikes the flower; yellow mid-vein, RHS 12B, with the outer sides of the tepals pink, RHS 65A. Lower Surface: Light-pink to pink, RHS 65C–RHS 62B. Sppotting or Marking: Spots and markings are present, brownish orange in color, RHS 34A.

*Pedicel.*—Length: Medium to long, depending on cultivation conditions. Color: RHS 141C. Form: Tapering like a lancet.

*Texture.*—Papillose.

*Disease resistance.*—Average in comparion to the disease resistance level of traditional Lily cultivars.

*Fragrance.*—Weak.

*Lasting quality.*—Excellent i.e., the average lasting period is at least 21 days, when cut and kept in a controlled climate in conformity with Dutch Auctions and Research Station standards.

Reproductive organs:

*Stamens and anthers.*—Arrangements: Anthers form a generally circular pattern at their upper ends. Number: 6. Length: Medium to long, depending on cultivation conditions. Filaments Color: Yellowish green RHS 145C.

*Pollen color.*—Brownish orange, RHS 34A.

*Anther color*—Brownish orange, RHS 34A.

*Pistils.*—Green RHS 141C.

*Stigma.*—Grey RHS 141D.

*Ovaries.*—Triangular in shape.

I claim:

1. A new and distinct cultivar of Lily plant named 'Lombardia', as illustrated and described herein.

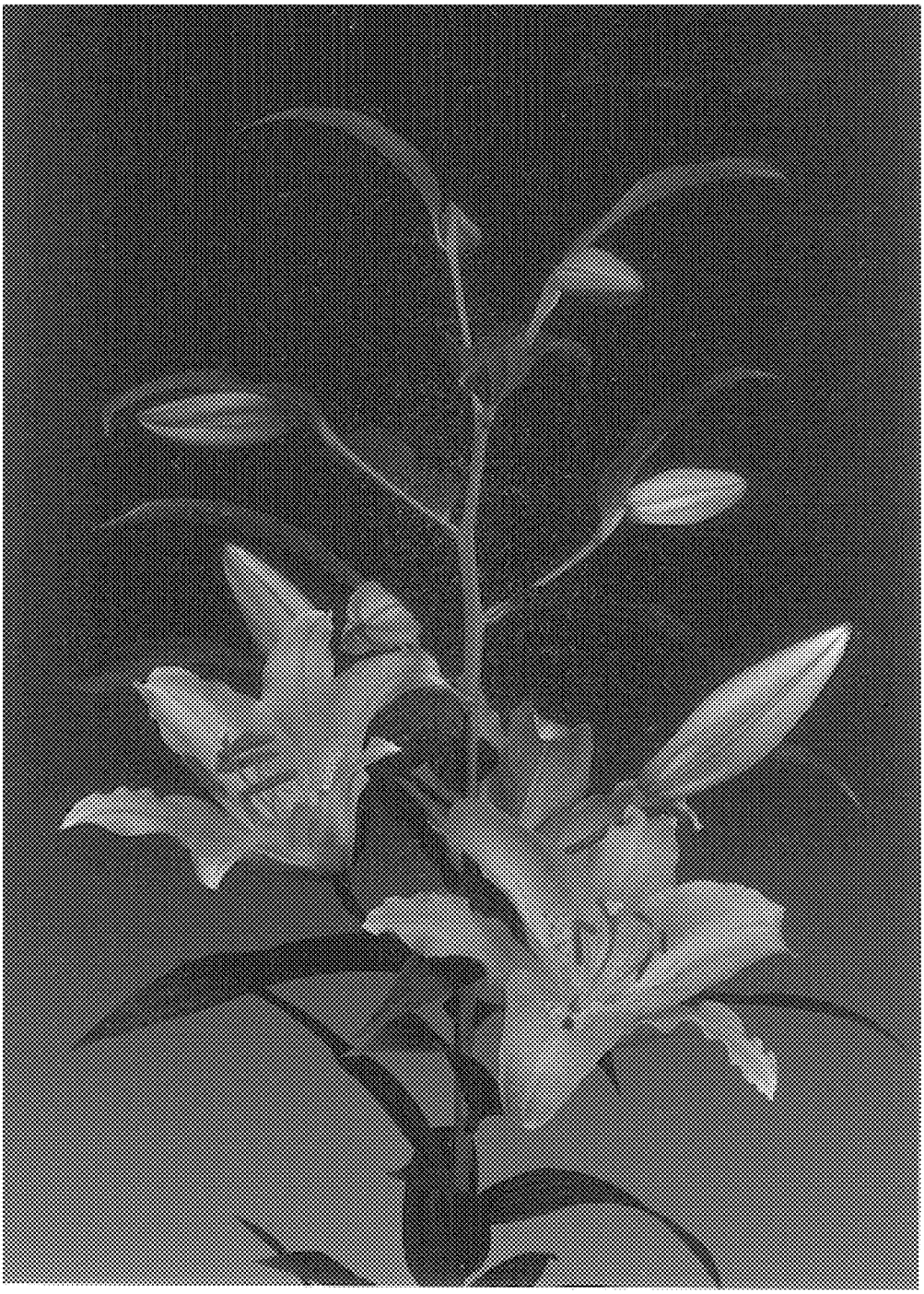

* * * * *